United States Patent
McGeehan et al.

(10) Patent No.: US 10,696,949 B2
(45) Date of Patent: Jun. 30, 2020

(54) SYSTEMS AND METHODS FOR CANINE LIVER MODELING

(71) Applicant: Hepregen Corporation, Medford, MA (US)

(72) Inventors: John K. McGeehan, Medford, MA (US); Stacy Krzyzewski, Medford, MA (US); Michael McVay, Boston, MA (US)

(73) Assignee: Ascendance Biotechnology, Inc., Medford, MA (US)

( * ) Notice: Subject to any disclaimer, the term of this patent is extended or adjusted under 35 U.S.C. 154(b) by 149 days.

(21) Appl. No.: 15/006,754

(22) Filed: Jan. 26, 2016

(65) Prior Publication Data

US 2016/0369238 A1    Dec. 22, 2016

Related U.S. Application Data

(60) Provisional application No. 62/107,878, filed on Jan. 26, 2015.

(51) Int. Cl.
*C12N 5/071* (2010.01)
*G01N 33/50* (2006.01)

(52) U.S. Cl.
CPC ....... *C12N 5/0671* (2013.01); *G01N 33/5067* (2013.01); *C12N 2500/99* (2013.01); *C12N 2501/12* (2013.01); *C12N 2502/1323* (2013.01); *C12N 2533/54* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 2006/0270032 A1* | 11/2006 | Bhatia | C12N 5/0671 435/325 |
| 2008/0220516 A1* | 9/2008 | Eddington | B01L 3/5025 435/305.2 |
| 2012/0216304 A1* | 8/2012 | Bhatia | A61L 27/18 800/9 |

* cited by examiner

*Primary Examiner* — Blaine Lankford
(74) *Attorney, Agent, or Firm* — Ballard Spahr LLP

(57) ABSTRACT

The present disclosure provides compositions, systems, and tools for modeling the canine liver and methods of using the same. The disclosure provides micropatterned hepatocyte co-cultures where individual cell populations remain functionally stable during long-term culture.

22 Claims, 11 Drawing Sheets
(10 of 11 Drawing Sheet(s) Filed in Color)

(Dog hepatocytes begin swelling at day 2)

SYSTEMS AND METHODS FOR CANINE LIVER MODELING

REFERENCE TO RELATED APPLICATIONS

This application claims the benefit of the filing date of U.S. Provisional application No. 62/107,878, filed Jan. 26, 2015. The disclosure of that application is incorporated by reference in its entirety.

BACKGROUND OF THE INVENTION

Liver failure is the cause of death of over 30,000 patients in the United States every year and over 2 million patients worldwide. Drug-induced liver disease is a major challenge for the pharmaceutical industry since unforeseen liver toxicity causes many new drug candidates to fail either in clinical trials or after release. In vitro cell culture techniques can be used to study human and animal hepatic tissue cells, and the effects of various drugs on the cells. Additionally, in vitro models can provide valuable information on drug uptake and metabolism, enzyme induction, and drug interactions affecting metabolism and hepatotoxicity. Micropatterned hepatocyte-stromal cell co-culture (MPCC) systems have been developed recently for culturing hepatocytes. One of the remarkable features of the MPCC technology is that for human, rat, and monkey hepatocytes, the cultures remain relatively phenotypically stable for at least a month. This is in contrast to prior technology such as monocultures of hepatocytes that are only stable for a week.

However, application of existing MPCC technology to canine hepatocyte cell culture causes early and extreme morphological changes to the architecture of the cell culture (loss of uniform island shape) and extreme hypertrophy of the hepatocytes. The morphological changes reduce confidence that the canine co-cultures are representative of in-vivo liver tissue. Therefore, the correlation of the existing canine co-culture with in-vivo canine livers is highly questionable. Thus, a need exists for improved canine co-cultures that can serve as reliable models of in-vivo canine livers.

SUMMARY OF THE INVENTION

In certain aspects, the disclosure provides a micropatterned co-culture comprising: (a) a population of canine hepatocytes defining a cellular island; and (b) a population of stromal cells, wherein the stromal cells define a geometric border of the cellular island, wherein the canine hepatocytes maintain long-term functional stability.

In certain aspects, the disclosure provides a micropatterned co-culture comprising: (a) a population of canine hepatocytes defining a cellular island, wherein the cellular island comprises a diameter or width of about 1 mm to 6 mm; and (b) a population of stromal cells, wherein the stromal cells define a geometric border of the cellular island, wherein the canine hepatocytes maintain long-term functional stability.

In certain aspects, the disclosure provides a method for producing a micropatterned co-culture containing canine hepatocytes, the method comprising: (a) spotting an adherence material on a substrate at spatially different locations, each spot having a defined geometric pattern, wherein the defined geometric pattern comprises a diameter or width of about 1 mm to 6 mm; (b) contacting the substrate with a population of canine hepatocytes that selectively adhere to the adherence material and/or substrate; (c) culturing the canine hepatocytes on the substrates to generate a plurality of cellular islands; and (d) contacting the substrate with a stromal cell population that adheres to the substrate at a location different than the hepatocyte population, wherein the cells of the stromal cell population define a geometric border of the cellular island, to generate a hepatocyte-stromal cell co-culture, wherein the canine hepatocytes maintain long-term functional stability.

In certain aspects, the disclosure provides a cellular composition made by the method disclosed herein.

In certain aspects, the disclosure provides a method of determining the interaction of one or more test compounds with canine hepatocytes comprising: a) contacting a micropatterned co-culture comprising canine hepatocytes and stromal cells with one or more test agents; and b) measuring a characteristic of the one or more test compounds or an activity of the hepatocytes, wherein the characteristic or activity measured in (b) indicates the interaction of one or more test compounds with hepatocytes, and wherein the hepatocytes maintain long-term functional stability.

In certain aspects, the disclosure provides a method of determining efficacy of one or more test agents comprising: a) contacting a micropatterned co-culture comprising canine hepatocytes and stromal cells with one or more test agents; and b) measuring an activity of the canine hepatocytes, wherein the activity measured in (b) indicates the efficacy of one or more test agents, and wherein the hepatocytes maintain long-term functional stability.

In certain aspects, the disclosure provides a method of determining metabolism of one or more test agents comprising: a) contacting a micropatterned co-culture comprising canine hepatocytes and stromal cells with one or more test agents; and b) measuring a characteristic of the one or more test agents or an activity of the canine hepatocytes, wherein the characteristic measured in (b) indicates the indicates the metabolism of one or more test agents, and wherein the hepatocytes maintain long-term functional stability In certain aspects, the disclosure provides a method of determining elimination of one or more test agents comprising: a) contacting a micropatterned co-culture comprising canine hepatocytes and stromal cells with one or more test agents; b) measuring a characteristic of the one or more test agents or an activity of the canine hepatocytes, wherein the characteristic or activity measured in (b) indicates the elimination of the one or more test agents, and wherein the hepatocytes maintain long-term functional stability In certain aspects, the disclosure provides a method of determining an interaction between two or more test agents comprising: a) contacting a micropatterned co-culture comprising canine hepatocytes and stromal cells with two or more co-administered test agents; b) measuring a characteristic of the test agents or an activity of the canine hepatocytes, wherein the characteristic or activity measured in (b) indicates the interaction of two or more test agents, and wherein the hepatocytes maintain long-term functional stability.

In certain aspects, the disclosure provides a method of selecting stromal cells for use in a micropatterned co-culture comprising canine hepatocytes, comprising detecting a stromal cell that does not induce canine hepatocyte hypertrophy in a micropatterned co-culture comprising the canine hepatocytes and the stromal cells.

In certain aspects, the disclosure provides a method of selecting stromal cells for use in a micropatterned co-culture comprising canine hepatocytes, comprising detecting a stromal cell that does not induce canine hepatocyte motility in a micropatterned co-culture comprising the canine hepatocytes and the stromal cells.

In some embodiments, the stromal cells do not induce canine hepatocyte hypertrophy or motility.

In some embodiments, the stromal cells secrete a level of hepatocyte growth factor (HGF) that does not induce canine hepatocyte hypertrophy. In some embodiments, the stromal cells secrete a level of HGF that does not induce canine hepatocyte motility. In some embodiments, the stromal cells exhibit a decreased production or secretion of HGF relative to 3T3-J2 murine fibroblasts.

In some embodiments, the cellular island comprises a diameter or width of about 1 mm to 6 mm. In some embodiments, the cellular island comprises a diameter or width of about 3 mm to 5 mm. In some embodiments, the cellular island comprises a diameter or width of about 3 mm.

In some embodiments, the micropatterned co-culture further comprises an HGF-inhibiting agent. In some embodiments, the HGF-inhibiting agent is selected from the group consisting of dexamethasone and TGFB2.

In some embodiments, the cellular islands maintain their shape during long-term culture. In some embodiments, the canine hepatocytes maintain their morphology during long-term culture.

In some embodiments, the stromal cells are fibroblast cells or fibroblast derived cells. In some embodiments, the stromal cells are human foreskin BJ fibroblasts. In some embodiments, the micropatterned co-culture further comprises one or more populations of non-parenchymal cells. In some embodiments, the one or more populations of non-parenchymal cells are Kupffer cells. In some embodiments, the one or more populations of non-parenchymal cells are selected from the group consisting of Ito cells, endothelial cells, biliary duct cells, immune-mediating cells, and stem cells. In some embodiments, the immune-mediating cells are selected from the group consisting of macrophages, T cells, neutrophils, dendritic cells, mast cells, eosinophils and basophils.

In some embodiments, the cellular islands are spaced apart from about 400 µm to 1000 µm from edge of one cellular island to the edge of an adjacent cellular island.

In some embodiments, the micropatterned co-culture is located in a microfluidic device. In some embodiments, the micropatterned co-culture is located in a tissue culture plate.

In some embodiments, the hepatocytes maintain long-term functional stability for at least 10 days. In some embodiments, the functional stability of the canine hepatocytes is determined by measuring an activity selected from gene expression, cell function, metabolic activity, morphology, and a combination thereof, of the hepatocytes. In some embodiments, the metabolic activity is selected from CYP3A4 (or corresponding canine gene) activity, urea synthesis, and albumin secretion.

In some embodiments, the stromal cells are selected from the group consisting of human cells, rat cells, mouse cells, monkey cells, dog cells, fish cells and guinea pig cells. In some embodiments, the non-parenchymal cells are selected from the group consisting of human cells, rat cells, mouse cells, monkey cells, dog cells, fish cells and guinea pig cells.

In some embodiments, the micropatterned co-cultures further comprise Kupffer cells. In some embodiments, the ratio of the Kupffer cells to the hepatocytes corresponds to the ratio of the cells in an inflamed state of the liver in canines. In some embodiments, the ratio of the Kupffer cells to the hepatocytes corresponds to the ratio of the cells in a physiologically normal state of the liver.

In some embodiments, the metabolic activity is protein production. In some embodiments, the metabolic activity is enzyme bioproduct formation. In some embodiments, the metabolic activity is a CYP450 isoenzyme activity. In some embodiments, the CYP450 isoenzyme is selected from the group consisting of CYP1A2, CYP1B1, CYP2A6, CYP2B6, CYP2C, CYP2D6, CYP2E1, CYP2F1, CYP2J2, CYP3A4, CYP4A, and CYP4B.

In some embodiments, the methods of the disclosure are used in determining inflammation-mediated toxicity of a test agent. In some embodiments, the methods of the disclosure are used in in determining inflammation-mediated effects on co-administered test agent combinations.

In some embodiments, the test agent is selected from the group consisting of a cytotoxic agent, pharmaceutical agent, a small molecule, and a xenobiotic.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
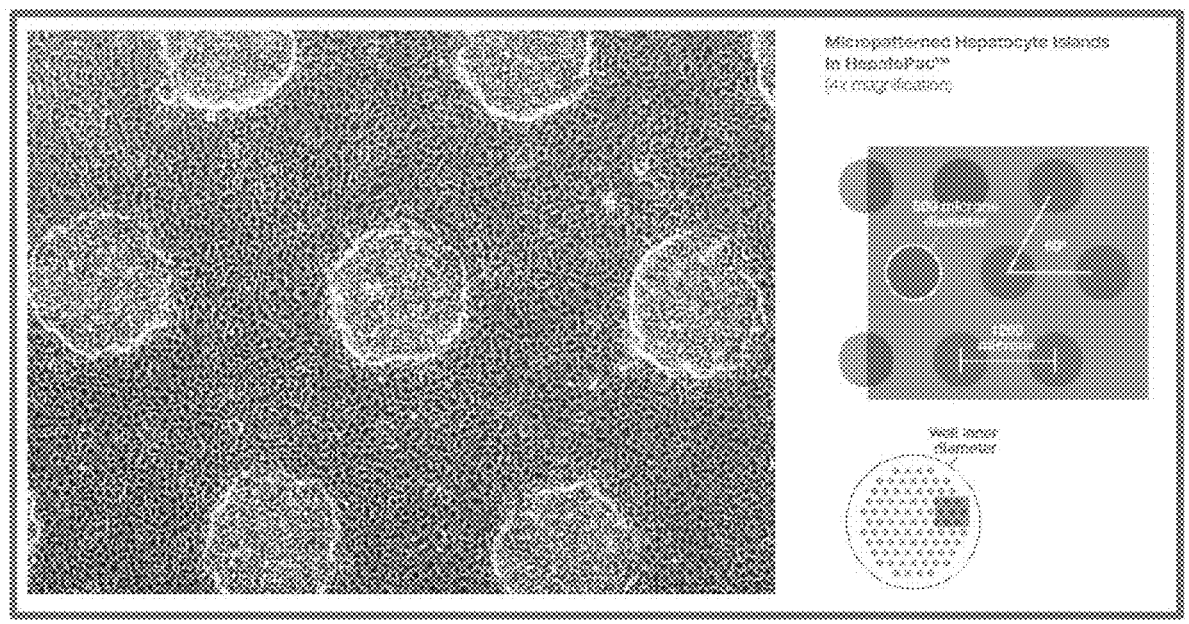
FIG. 1 shows the HepatoPac™ platform. HepatoPac™ architecture used for human, monkey, and rat hepatocytes consists of 500 µm hepatocyte islands, spaced 1200 µm apart (center-to-center). 3T3-J2 murine fibroblasts are used as stromal cells for human, rat and monkey formats.

The present disclosure provides compositions, systems, and tools for modeling the canine liver and methods of using the same.

(i) Overview

Historically cell culture techniques and tissue development failed to take into account the necessary microenvironment for cell-cell and cell-matrix communication as well as an adequate diffusional environment for delivery of nutrients and removal of waste products. Cell culture techniques and understanding of the complex interactions cells have with one another and the surrounding environment have improved in the past decade.

While many methods and bioreactors have been developed to grow tissue for the purposes of generating artificial tissues for transplantation or for toxicology studies, these bioreactors do not adequately simulate, in vitro, the mechanisms by which nutrients, gases, and cell-cell interactions are delivered and performed in vivo. For example, cells in living tissue are "polarized" with respect to diffusion gradients. Differential delivery of oxygen and nutrients, as occurs in vivo by means of the capillary system, controls the relative functions of tissue cells and their maturation. Thus, cell culture systems and bioreactors that do not simulate these in vivo delivery mechanisms do not provide a sufficient corollary to in vivo environments to develop tissues or measure tissue responses in vitro.

Drug-induced liver disease represents a major economic challenge for the pharmaceutical industry since unforeseen liver toxicity and poor bioavailability issues cause more than 50% of new drug candidates to fail in Phase I clinical trials. Also, a third of drug withdrawals from the market and more than half of all warning labels on approved drugs are primarily due to adverse affects on the liver. Therefore, besides pharmacological properties, ADME/Tox (absorption, distribution, metabolism, excretion and toxicity) characteristics are crucial determinants of the ultimate clinical success of a drug. This realization has led to an early introduction of ADME/Tox screening during the drug discovery process, in an effort to select against drugs with problematic properties.

Incorporating in vitro models of human and animal livers into drug development provides several advantages: earlier elimination of problematic drugs, reduction in variability by allowing hundreds of experiments per animal and human models without patient exposure. In the case of the liver, in vitro models can provide valuable information on drug uptake and metabolism, enzyme induction, and drug-drug interactions affecting metabolism and hepatotoxicity.

Several in vitro liver models are used for short-term (hours) investigation of xenobiotic metabolism and toxicity. Perfused whole organs, liver slices and wedge biopsies maintain many aspects of liver's in vivo microenvironment; however, such systems suffer from limited drug availability to inner cell layers, limited viability (<24 h) and are not suitable for enzyme induction studies. Isolated liver microsomes, which are cellular fragments that contain mostly CYP450 enzymes, are used primarily to investigate drug metabolism via the phase I pathways (oxidation, reduction, hydrolysis and the like). However, microsomes lack many important aspects of the cellular machinery where dynamic changes occur (i.e. gene expression, protein synthesis) to alter drug metabolism, toxicity and drug-drug interactions. Besides microsomes, cell lines derived from hepatoblastomas (HepG2) or from immortalization of primary hepatocytes (HepLiu, SV40 immortalized) are finding limited use as reproducible, inexpensive models of hepatic tissue. However, no cell line has been developed to date that maintains physiologic levels of liver-specific functions. Usually such cell lines are plagued by an abnormal repertoire of hepatic functions.

Current in vitro liver models used by the pharmaceutical industry, though useful in a limited capacity, are not fully predictive of in vivo liver metabolism and toxicity. Thus, research has increasingly turned towards using isolated primary hepatocytes as the gold standard for in vitro studies; however, hepatocytes are notoriously difficult to maintain in culture as they rapidly lose viability and phenotypic functions.

The invention provides methods, tools, and compositions that overcome the limitations of current techniques. The disclosure provides stable micropatterned canine hepatocyte co-cultures for modeling the canine liver in vitro. The co-cultures of the invention have distinct advantages over current in-vitro 3-D model liver systems in terms of simplicity, ease of use, adaptability and scalability for high-throughput applications. In addition, the canine hepatocytes of the co-culture maintain functional stability during long-term culturing. This unexpected property facilitates the implementation and development of assays, such as long-term evaluation of drug toxicity profiles, which were not feasible earlier due to limited cell functionality.

(ii) Definitions

For convenience, certain terms employed in the specification, examples, and appended claims are collected here.

As used herein, the singular forms "a," "and," and "the" include plural referents unless the context clearly dictates otherwise. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

As used herein, the term "micropattern" refers to a pattern formed on a substrate (e.g., by a protein, cell, or combination of cells of two or more types), which has a spatial resolution (e.g., 1-5 μm) that permits spatially controlling cell placement at the single-cell level. Thus, using micropatterning methods, one can precisely manipulate cell-cell interactions.

A cellular island or "spot" refers to a bounded geometrically defined shape of a substantially homogenous cell-type having a defined border. In one aspect, the cellular island or spot is surrounded by different cell-types, materials (e.g., extracellular matrix materials) and the like. The cellular islands can range in size and shape (e.g., may be of uniform dimensions or non-uniform dimensions). Cellular islands may be of different shapes on the same substrate. Furthermore, the distance between two or more cellular islands can be designed using methods known in the art (e.g., lithographic methods and spotting techniques). The distances between cellular islands can be random, regular or irregular. The distance between and/or size of the cellular islands can be modified to provide a desired phenotypic characteristic of morphology to a particular cell types (e.g., a parenchymal cell such as a hepatocyte).

(iii) Micropatterned Canine Hepatocyte Co-Cultures

The invention provides micropatterned canine hepatocyte-stromal cell co-cultures. The micropatterned configurations (from single cellular islands to large aggregates) outperform randomly distributed co-cultures. Amongst the micropatterned configurations that were engineered, a balance of homotypic and heterotypic interactions can yield functional co-cultures having defined or desired phenotypic activity, longevity and proliferative capacity.

The morphology and function of cells in an organism vary with respect to their environment, including distance from sources of metabolites and oxygen as well as homotypic and heterotypic cell interactions. For example, the morphology and function of hepatocytes are known to vary with position along the liver sinusoids from the portal triad to the central vein (Bhatia et al., Cellular Engineering 1:125-135, 1996; Gebhardt R. Pharmaol Ther. 53 (3):275-354, 1992; Jungermann K. Diabete Metab. 18 (1):81-86, 1992; and Lindros, K. O. Gen Pharmacol. 28 (2):191-6, 1997). This phenomenon, referred to a zonation, has been described in virtually all areas of liver function. Oxidative energy metabolism, carbohydrate metabolism, lipid metabolism, nitrogen metabolism, bile conjugation, and xenobiotic metabolism, have all been localized to separate zones. Such compartmentalization of gene expression is thought to underlie the liver's ability to operate as a 'glucostat' as well as the pattern of zonal hepatotoxicity observed with some xenobiotics (e.g., environmental toxins, chemical/biological warfare agents, natural compounds such as holistic therapies and nutraceuticals).

Isolated human and animal parenchymal cells (such as hepatocytes) are highly unstable in culture and are therefore of limited utility for studies on drug toxicity, drug-drug interaction, drug-related induction of detoxification enzymes, and other phenomena. In spite of their recognized advantages, primary parenchymal cells are notoriously difficult to maintain in culture as they rapidly lose viability and phenotypic functions upon isolation from their in vivo microenvironment. Isolated hepatocytes rapidly lose important liver-specific functions such as albumin secretion, urea synthesis and cytochrome P450 activity. After about a week in culture on collagen-coated dishes, hepatocytes show a fibroblastic morphology. Freshly isolated hepatocytes, on the other hand, show a polygonal morphology with distinct nuclei and nucleoli and bright intercellular boundaries (bile canaliculi). De-differentiated hepatocytes are typically unresponsive to enzyme inducers, which severely limits their use.

Over the last couple of decades, investigators have been able to stabilize several hepatocyte functions using soluble factor supplementation, extracellular matrix manipulation, and random co-culture with various liver and non-liver derived stromal cell types. Addition of low concentrations of hormones, corticosteroids, cytokines, vitamins, or amino acids can help stabilize liver-specific functions in hepatocytes. Presentation of extracellular matrices of different composition and topologies can also induce similar stabilization. For instance, hepatocytes from a variety of species (human, mouse, rat) secrete albumin when sandwiched between two layers of rat tail collagen-I (double-gel). However, studies have shown that CYP450 activities decline in the double-gel model, and the presence of an overlaid layer of collagen presents transport barriers for drug candidates, thus limiting their use as assay systems. Culture on a tumor-derived basement membrane extract called Matrigel also induces hepatocyte spheroid formation and leads to retention of key hepatocyte functions including P450 activity. While Matrigel can induce functions in rodent hepatocytes, it appears to have fewer effects on human hepatocytes. Though they may find use in specific scenarios during drug discovery and development, most in vitro liver models in use have limited applicability to the development of a robust biomimetic liver platform. For instance, defined media formulations limit the contents of the perfusate, sandwich culture adds a transport barrier and hepatocytes do not express gap junctions, and Matrigel and spheroid culture rely on hepatocyte aggregation with resultant non-uniformity and transport barriers.

The invention overcomes many of these problems by optimizing the homotypic and heterotypic interactions of parenchymal cells with non-parenchymal cells. For example, in the adult liver, hepatocytes interact with a variety of non-parenchymal cell types including sinusoidal endothelia, stellate cells, Kupffer cells and fat-storing Ito cells (e.g., heterotypic interactions). These non-parenchymal cell types modulate cell fate processes of hepatocytes under both physiologic and pathophysiologic conditions. In vitro, random co-cultivation of primary hepatocytes with a plethora of distinct non-parenchymal cell types from different species and organs has been shown to support differentiated hepatocyte function for several weeks in a manner reminiscent of hepatic organogenesis. These random hepatocyte co-cultures have been used to study various aspects of liver physiology and pathophysiology such as lipid metabolism, and induction of the acute-phase response.

The liver contains several resident cell types in addition to hepatocytes, including stellate cells, cholangiocytes, oval cells, Kupffer cells, and sinusoidal endothelial cells. In the adult liver, the majority of liver cells are hepatocytes, with stellate cells and cholangiocytes representing minority populations of cells. Stellate cells function as the primary source of extracellular matrix in normal and diseased liver, transitioning from a quiescent vitamin-A rich cell to a highly fibrogenic cell during activation caused by liver injury. Cholangiocytes line the intrahepatic biliary tree inside the liver. Cholangiocytes play a key role in the modification of bile, secreted by hepatocytes, by a series of reabsorbtive and secretory processes under both spontaneous and hormoneregulated conditions. Cholangiocytes also have the ability to selectively proliferate during injury such as bile duct ligation. Oval cells are found in the periportal region of the liver under some conditions, and have been postulated to function as a bi-potential precursor cell with the ability to give rise to hepatocytes and cholangiocytes (also known as bile duct cells).

An exemplary micropatterned bi-culture is the HepatoPac™, which provides, in a multi-well format (e.g., up to 96-well or up to 384-well), in vitro models of human and animal (i.e. rat, dog, monkey) livers (Khetani and Bhatia, Nat Biotechnol. 26(1):120-126, 2007). Primary hepatocytes are organized into colonies of prescribed, empirically-optimized dimensions and subsequently surrounded by supportive stromal cells. Hepatocytes in HepatoPac™ retain their in vivo-like morphology, express a complete complement of liver-specific genes, metabolize compounds using active Phase I/II drug metabolism enzymes, secrete diverse liver-specific products, and display functional bile canaliculi for 4-6 weeks in vitro (Wang et al. Drug Metab Dispos. 38(10):1900-1905, 2010). The balance of homotypic and heterotypic interactions between hepatocytes and stromal cells is very important for the long-term functional stability of hepatocytes in bi-culture. One of the remarkable features of the micropatterned co-culture (MPCC) technology is that for human, rat, and monkey hepatocytes the cultures remain relatively phenotypically stable for at least a month. This is in contrast to prior technology such as monocultures of hepatocytes that are only stable for a week. The co-cultures mentioned above are considered phenotypically stable because, following several initial days of culture maturation, the shape of hepatocyte islands as well as the morphology of individual hepatocytes do not change significantly during the life of the culture. Along with this morphological stability, biological markers of hepatocyte functionality such as albumin, urea and liver specific enzymes such as cytochrome P450 CYP3A are maintained at high levels.

In contrast, application of existing MPCC technology to Canine hepatocyte cell culture causes early and extreme morphological changes to the architecture of the cell culture (loss of uniform island shape) and extreme hypertrophy of the hepatocytes. Although biological markers indicative of hepatocyte functionality were detected in Canine co-cultures that lost segregation into islands and hypertrophy of hepatocytes, the morphology change reduces confidence that the canine co-cultures are representative of in-vivo liver tissue. Therefore, correlation of the existing canine co-culture with in-vivo canine livers is highly questionable.

In the current invention, a biological marker implicated as one of the contributing factors causing canine hepatocyte hypertrophy and motility in the co-culture was identified. This biological marker was used to help screen for an alternative to the 3T3-J2 murine fibroblasts used in the Human, Rat, and Monkey MPCC's. Human foreskin BJ epithelial cells were found to have low production of HGF, which was identified as one of the biological markers, and also found to reduce hypertrophy in the co-cultures while maintaining even higher levels of functionality as shown by CYP3A levels. Finally, increasing the diameter of the islands in the co-culture, alone or in addition to switching to the BJ stromal cells allowed the co-cultures to maintain a stable architecture, eliminating hepatocyte hypertrophy for the vast majority of canine hepatocytes, and maintain much higher levels of biological functionality than the prior MPCC architecture with 3T3-J2 murine stromal cells.

It will be recognized that HGF is a biological marker for all growth factors that can affect hypertrophy and motility and that other growth factors can be expected to have a similar effect. Therefore, in one aspect of the invention, stromal cell populations can be screened for their ability to not induce canine hepatocyte hypertrophy or motility. In some embodiments, the stromal cells secrete a level of hepatocyte growth factor (HGF) that does not induce canine hepatocyte hypertrophy. In some embodiments, the stromal cells secrete a level of HGF that does not induce canine hepatocyte motility. In some embodiments, the stromal cells exhibit a decreased production or secretion of HGF relative to 3T3-J2 murine fibroblasts.

The invention provides micropatterned cultures comprising cellular islands of parenchymal cells such as canine hepatocytes, surrounded by stromal cells. Optionally, one or more populations of non-parenchymal cells are additionally present. Microtechnology tools are used to both optimize and miniaturize in vitro models of human and animal livers. The micropatterned co-cultures are able to maintain functional stability during long-term culture. In this aspect, a substrate is modified and prepared such that the stromal cells and non-parenchymal cells are interspersed with islands of parenchymal cells, such as canine hepatocytes. Using microfabrication techniques modified, for example, from the semiconductor industry, the substrate is modified to provide for spatially arranging parenchymal cells (e.g., canine hepatocytes) and supportive stromal cells (e.g., fibroblasts) and one or more populations of non-parenchymal cells in a miniaturizable format. The spatial arrangements can be a parenchymal cell type comprising a bounded geometric shape. The bounded geometric shape can be any shape (e.g., regular or irregular) having dimensions defined by the shape (e.g., diameter, width, length and the like). The dimensions will have a defined scale based upon their shape such that at least one distance from one side to a substantially opposite side is about 1 mm-6 mm (e.g., where the shape is rectangular or oval, the distance between one side to an opposite side is 1-6 mm). The cellular islands may be spaced apart 400 µm to 1000 µm from edge to edge of the cellular islands. For example, parenchymal cells (e.g., canine hepatocytes) can be prepared in circular islands of varying dimensions (e.g., 500 µm, 750 µm, 1 mm, 2 mm, 3 mm, 4 mm, 5 mm, 6 mm, 7 mm, or 8 mm; typically about 1 to 6 mm with about 400 to 1000 µm spacing) surrounded by stromal cells (e.g., fibroblasts such as murine 3T3 fibroblasts or human BJ fibroblasts) and optionally, one or more populations of non-parenchymal cells (e.g., Kupffer cells).

One drawback of existing canine hepatic co-culture technologies is the inability of the hepatocytes to maintain functional stability during long-term culture. The inventors have found that increasing the island size and switching to stromal cell populations that do not induce canine hepatocyte hypertrophy and motility in the micropatterned HepatoPac™ format, allows canine hepatocytes to maintain optimal functional stability for a greater length of time. In some embodiments, the canine hepatocytes maintain functional stability in the micropatterned co-culture for at least 10 days. In some embodiments, the canine hepatocytes maintain functional stability in the tri-culture for at least 4, 5, 6, 7, 8, 9, 10, 11, 12, 13, 14, 15, 16, 17, 18, 19, 20, 21, 22, 23, 24, 25, 26, 27, 28, 29, or 30 days. In some embodiments, the canine hepatocytes maintain functional stability for at least 4-10, at least 4-11, at least 4-12, at least 4-13, at least 4-14, at least 5-10, at least 5-11, at least 5-12, at least 5-13, at least 5-14, at least 6-10, at least 6-11, at least 6-12, at least 6-13, at least 6-14, at least 7-10, at least 7-11, at least 7-12, at least 7-13, at least 7-14, at least 10-15, at least 15-20, at least 20-22, at least 20-25, at least 22-30, or at least 25-30 days. In some embodiments, the canine hepatocytes maintain functional stability for about 4-10, about 4-11, about 4-12, about 4-13, about 4-14, about 5-10, about 5-11, about 5-12, about 5-13, about 5-14, about 6-10, about 6-11, about 6-12, about 6-13, about 6-14, about 7-10, about 7-11, about 7-12, about 7-13, at least 7-14, at least 10-15, at least 15-20, at least 20-22, at least 20-25, at least 22-30, or at least 25-30 days. In some embodiments, the canine hepatocytes maintain functional stability up to 14, 15, 16, 17, 18, 19, 20, 21, 22, 23, 24, 25, 26, 27, 28, 29, or 30 days. Functional stability of hepatocytes may be determined by measuring hepatocyte specific functions such as, but not limited to CYP450 expression or activity, urea synthesis, and albumin secretion. Various hepatocyte specific assays are known in the art and can be employed to evaluate the functional stability of canine hepatocytes in culture. Advantages of the co-cultures disclosed herein include evaluating long-term drug metabolism and toxicity profiles.

Non-parenchymal cells which may be added to the micropatterned hepatic co-cultures include, but are not limited to, liver cells such as Kupffer cells, Ito cells, sinusoidal endothelial cells, biliary duct cells, immune cells such as macrophages, T cells, neutrophils, dendritic cells, mast cells, eosinophils, and basophils, and stem cells such as liver progenitor cells, oval cells, hematopoietic stem cells, embryonic stem cells. The non-parenchymal cells may be primary cells, or they may be derived from an established cell line. The cell populations of the co-culture can be derived from one or more species. The cells may be mammalian cells, such as but not limited to human cells, rat cells, mouse cells, monkey cells, pig cells, dog cells, and guinea pig cells. In some embodiments, the cells are other vertebrate cells such as but not limited to, fish cells including zebrafish cells, or *Xenopus* cells. The cells may be fresh or cryopreserved.

The stromal cells may be cells that have intrinsic attachment capabilities, thus eliminating a need for the addition of serum or exogenous attachment factors. Some cell types will attach to electrically charged cell culture substrates and will adhere to the substrate via cell surface proteins and by secretion of extracellular matrix molecules. The stromal cells may be fibroblasts (e.g., normal or transformed fibroblasts, such as NIH 3T3-J2 cells).

The stromal cells can be primary cells, or they may be derived from an established cell line. The cell populations of the co-culture can be derived from one or more species. The cells may be mammalian cells, such as but not limited to human cells, rat cells, mouse cells, monkey cells, pig cells, dog cells, and guinea pig cells. In some embodiments, the cells are other vertebrate cells such as but not limited to, fish cells including zebrafish cells, or *Xenopus* cells. The cells may be fresh or cryopreserved.

In some embodiments, the micropatterned co-cultures are present in a multi-well format of up to 96-wells. In some embodiments, the micropatterned co-cultures are present in a multi-well format of up to 384-wells. In some embodiments, the micropatterned co-culture is located in a microfluidic device. In some embodiments, the micropatterned co-culture is located in tissue culture plate.

(iv) In Vitro Model of Canine Liver

The micropatterned co-cultures of the invention are useful in drug discovery and development including screening for metabolic stability, drug-drug interactions, and toxicity. Metabolic stability is a key criterion for selection of lead drug candidates that proceed to preclinical trials. The in vitro canine liver model of the invention is useful in understanding drug metabolism, toxicity and drug-drug interactions. In one aspect, the in vitro canine liver model of the invention is useful for long-term evaluation of the effects of inflammation-mediated drug toxicity.

It will be recognized that non-canine hepatocytes may be used in the invention to facilitate identification of properties or metabolisms suitable for further study of such cells. Non-canine cell types include but are not limited to rat, mouse, monkey, pig, guinea pig, fish, and *Xenopus*. This information can then be used to deduce the mechanism by which the metabolites are generated, with the ultimate goal of focusing clinical studies. Though there are quantitative differences, there is good in vivo to in vitro correlation in drug biotransformation activity when isolated hepatocytes are used. Metabolite profiles obtained via canine hepatocyte in vitro models can also be used to choose the appropriate animal species to act as the canine surrogate for preclinical pharmacokinetic, pharmacodynamic and toxicological studies. Studies have shown that interspecies variations are retained in vitro and are different depending on the drug being tested.

The validation of canine hepatocyte co-cultures as appropriate liver models for drug development includes cell-based acute and chronic toxicity assays using a variety of clinical and non-clinical compounds, as well as induction and inhibition of key CYP450 enzymes.

In some embodiments, the disclosure provides methods of determining the inflammation-mediated effects on compound-hepatocyte interactions, including but not limited to, determining inflammation-mediated effects on metabolic stability, drug-drug interactions, and toxicity.

The co-cultures of the disclosure may be used to in vitro to screen a wide variety of compounds, such as cytotoxic compounds, growth/regulatory factors, pharmaceutical agents, and the like, to identify agents that modify cell (e.g., hepatocyte) function and/or cause cytotoxicity and death or modify proliferative activity or cell function. In some embodiments, the co-cultures of the disclosure may be used to screen a wide variety of compounds, such as cytotoxic compounds, growth/regulatory factors, pharmaceutical agents, and the like, to identify agents that modify cell (e.g., hepatocyte) function and/or cause cytotoxicity and death or modify proliferative activity or cell function whose metabolic, toxicity and/or drug-drug interaction profiles are significantly altered by inflammation. In some embodiments, the co-cultures are used to identify compounds that have the potential to exhibit idiosyncratic liver toxicity. For example, the culture system may be used to test absorption, distribution, metabolism, excretion, and toxicology (ADMET) of various agents in the presence or absence of inflammation. To this end, the cultures are maintained in vitro comprising a defined cellular island geometry and exposed to a compound to be tested. The activity of a compound can be measured by its ability to damage or kill cells in culture or by its ability to modify the function of the cells (e.g., in hepatocytes the expression of P450, and the like). This may readily be assessed by vital staining techniques, ELISA assays, immunohistochemistry, and the like. The effect of growth/regulatory factors on the cells (e.g., hepatocytes) may be assessed by analyzing the cellular content of the culture, e.g., by total cell counts, and differential cell counts or by metabolic markers such as MTT and XTT. This may also be accomplished using standard cytological and/or histological techniques including the use of immunocytochemical techniques employing antibodies that define type-specific cellular antigens.

In one aspect, the activity of a compound can be measured by its effect on gene expression, cell function, metabolic activity, morphology, or a combination thereof, of the hepatocytes of the co-culture. In some embodiments, the metabolic activity is Phase I or Phase II enzyme activity, urea synthesis, or albumin secretion. In some embodiments, the effect on CYP450 expression or activity is measured. In some embodiments, the CYP450 isoenzyme is CYP3A4. Exemplary CYP450 isoenzymes include CYP1A2, CYP1B1, CYP2A6, CYP2B6, CYP2D6, CYP2E1, CYP2F1, CYP2J2, CYP3A4, CYP4A, and CYP4B. Exemplary CYP450 isoenzymes are described in U.S. Pat. No. 8,217,161, the disclosure of which is incorporated herein by reference in its entirety. In some embodiments, the effect on hepatic uptake is measured. In some embodiments, effect on cell function is assessed by measuring ATP levels. In some embodiments, cytokine secretion is measured. Cytokine arrays may be used to measure cytokine release. In some embodiments protein secretion is analyzed. To detect the modulation of a metabolic or synthetic function, conventional molecular and biochemical assays can be used. For example, suitable in vitro assays can include assays to analyze hepatocyte proliferation, e.g., via BrdU incorporation; hepatocyte apoptosis, for example, by analyzing morphological changes associated with apoptosis/necrosis, or by using, e.g., TUNEL assay; RT-PCR to detect alterations in the mRNA expression levels of IL-10, IL-6, HGF, EGF, and TNF-α, ELISA to detect altered IL-10, TNF-α, IL-1β, IL-6, IL-2, IL-1ra expression.

In one aspect, characteristics of a compound are measured in the presence or absence of inflammation. In some embodiments, metabolic stability of a compound is measured. In some embodiments, presence or absence of metabolites is measured. In some embodiments, the compound may be detectably labeled, for example, the compound may be radiolabeled. Methods for measuring characteristics of compounds, such as mass spectrometry, are well known in the art.

The cytotoxicity to cells in culture (e.g., canine hepatocytes) of pharmaceuticals, anti-neoplastic agents, carcinogens, food additives, and other substances may be tested by utilizing the co-culture system of the disclosure in the presence or absence of inflammation. In certain embodiments, toxicity may be mediated by TNF-α or IL-6. In certain embodiments, toxicity may be mediated by TNF-α, TNF-β, IL-1, IL-6, IL-8, IL-12, IL-15, IL-18, MIP-1α, MIP-1βMCP-1, IFNγ, IL-2, IFNα/β, lymphotoxinαβ, LIGHT, CD40L, FasL, CD30L, CD27L, 4-1BBL, Ox40L, CD120α, or CD120β.

In one aspect, cytotoxicity is measured by generating a dose-response curve to determine the 50% toxic concentration (TC50) value. The length of dosing and the range of dosing concentrations will vary depending on the compound. In one embodiment, the cultures are dosed with the compounds at multiples of the maximum plasma concentration (Cmax) of the compound. In one embodiment, cytoxicity is determined by measuring cellular ATP content. In some embodiments, cytotoxicity is determined by total cell counts, and differential cell counts or by metabolic markers such as MTT and XTT, Resazurin conversion, or alamarBlue assay (Life Technologies). In one aspect, cytotoxicity in the presence or absence of inflammation is determined to determine if cytotoxicity is potentiated by inflammation. In one embodiment, cytotoxicity may be potentiated by inflammation if the TC50 value in the presence of inflammation is lowered by at least 20%, at least 30%, at least 40%, at least 50%, at least 60%, at least 70%, at least 80%, or at least 90%. In some embodiments, the TC50 value in the presence of inflammation is lowered by 20-35%, 35-50%, 50-65%, 65-80%, or 80-90%.

In one aspect of the assay system, a stable, growing culture is established having a desired size (e.g., island size and distance between islands), morphology and may also include a desired oxygen gradient. The cells/tissue in the culture are exposed to varying concentrations of a test agent. After incubation with a test agent, the culture is examined by phase microscopy or by measuring cell specific functions (e.g., hepatocyte cell indicators) such as protein production/metabolism to determine the highest tolerated dose—the concentration of test agent at which the earliest morphological abnormalities appear or are detected. Cytotoxicity testing can be performed using a variety of supravital dyes to assess cell viability in the culture system, using techniques known to those skilled in the art.

Once a testing range is established, varying concentrations of the test agent can be examined for their effect on viability, growth, and/or morphology of the different cell types.

In one aspect, the micropatterned co-cultures of the invention can be scaled-up to form a high-throughput microreactor array to allow for interrogation of xenobiotics. In one aspect, a microfluidic device is contemplated that has micropatterned co-culture areas in or along a fluid flow path.

Similarly, the beneficial effects of drugs may be assessed using the culture system in vitro; for example, growth factors, hormones, drugs which enhance hepatocyte formation or activity can be tested. In this case, stable micropattern cultures may be exposed to a test agent. After incubation, the micropattern cultures may be examined for viability, growth, morphology, cell typing, and the like as an indication of the efficacy of the test substance. Varying concentrations of the drug may be tested to derive a dose-response curve.

The culture systems of the invention may be used as model systems for the study of physiologic or pathologic conditions. For example, in a specific embodiment, the culture system can be optimized to act in a specific functional manner as described herein by modifying the size or distribution of cellular islands. In another aspect, the oxygen gradient is modified along with the density and or size of a micropattern of cells in the culture system.

One advantage of the culture systems of the disclosures is that the cells in such a culture system are substantially homogenous and autologous (e.g., the cellular islands are substantially homogenous and autologous) so you can do many experiments on the same biological background. In vivo testing, for example, suffers from animal-to-animal variability and is limited by the number of conditions or agents that can be tested on a given subject.

The compounds to be tested in the methods of the disclosure include, but are not limited to, pharmaceutical agents, pharmaceuticals, anti-neoplastic agents, carcinogens, food additives, xenobiotics, and cytotoxic agents. In some embodiments, the test compound is a small molecule, protein, protein fragment, or peptide. In some embodiments, the test compound is a small molecule of MW 1000-2000, MW 2000-2500, MW 2500-3000.

(v) Methods of Micropatterning

Methods of micropatterning useful to develop co-cultures with desired characteristics are described in U.S. Pat. No.

6,133,030 and U.S. Patent Application No. 2006-0270032, the disclosures of which are incorporated herein by reference in their entirety.

The cellular islands can take any geometric shape having a desired characteristic and can be defined by length/width, diameter and the like, based upon their geometric shape, which may be circular, oval, square, rectangular, triangular and the like. Furthermore, parenchymal cell (e.g. hepatocyte) function may be modified by altering the pattern configuration (e.g., the distance or geometry of the array of cellular islands). The distance between bounded geometric islands of cells may vary in a culture system (e.g., the distances between islands may be regular or irregular). Using techniques described herein, the spatial distances between cellular islands may be random, regular or irregular. Furthermore, combinations of geometric bounded areas (e.g., cellular islands) of different geometries (e.g., multiple island sizes) may be present on a single substrate with varying distances (e.g., multiple island spacings) or regular distances between the islands. In other words, the invention contemplates the use of cellular islands comprising various geometries and distances on a substrate (e.g., cocultures comprising cellular islands with 1 mm to 6 mm islands that are intermixed and regularly distributed). In one aspect, the cellular islands comprise a diameter or width from about 1 mm to 6 mm. Similarly, where the geometric island comprises a rectangle, the width can comprise about 1 mm to 6 mm. In another aspect, the canine hepatocyte cellular islands are spaced apart from one another by about 2 µm to 1500 µm from edge to edge of the cellular islands. In yet a further aspect, the canine hepatocyte cellular islands comprise a defined width (e.g., 1 mm to 6 mm) that can run the length of a culture area or a portion of the culture area. Parallel islands of parenchymal cells can be separated by parallel rows of stromal cells. In another aspect, the geometric shape may comprise a 3-D shape (e.g., a spheroid). In such instances, the diameter/width and the like, will be from about 1 mm to 6 mm. Additional non-parenchymal cells can be seeded at multiple ratios to allow balance of homotypic (hepatocyte/hepatocyte) and heterotypic (hepatocyte/stroma or hepatocyte/Kupffer cell) interactions in the micropatterned co-culture.

In some embodiments, the canine hepatocyte cellular islands have a width or diameter of about 500 µm, 750 µm, 1 mm, 2 mm, 3 mm, 4 mm, 5 mm, 6 mm, 7 mm, or 8 mm. In some embodiments, the canine hepatocyte cellular islands have a width or diameter ranging from about 500-750 µm, 750-1000 µm, 1 mm-3 mm, 2 mm-4 mm, 4 mm-6 mm. In some embodiments, the canine hepatocyte cellular islands have a width or diameter of about 3 mm.

As will be recognized in the art, the cellular islands may be present in any culture system including static and fluid flow reactor systems (e.g., microfluidic devices). Such microfluidic devices are useful in the rapid screening of agents where small flow rates and small reagent amounts are required.

The cellular culture of the invention can be made by any number of techniques that will be recognized in the art. For example, a method of making a plurality of cellular islands on a substrate can comprise spotting or layering an adherence material (or plurality of different cell specific adherence materials) on a substrate at spatially different locations each spot having a defined size (e.g., diameter) and spatial arrangement. The spots on the substrate are then contacted with a first cell population or a combination of cell types and cultured to generate cellular islands. Where difference cell-types are simultaneously contacted with the substrate, the substrate, coating or spots on the substrate will support cell-specific binding, thus providing distinct cellular domains. Methods for spotting adherence material (e.g., extracellular matrix material) can include, for example, robotic spotting techniques and lithographic techniques.

Various culture substrates can be used in the methods and systems of the invention. Such substrates include, but are not limited to, glass, polystyrene, polypropylene, stainless steel, silicon and the like. The choice of the substrate should be taken into account where spatially separated cellular islands are to be maintained. The cell culture surface can be chosen from any number of rigid or elastic supports. For example, cell culture material can comprise glass or polymer microscope slides. In some aspect, the substrate may be selected based upon a cell type's propensity to bind to the substrate.

The cell culture surface/substrate used in the methods and systems of the invention can be made of any material suitable for culturing mammalian cells. For example, the substrate can be a material that can be easily sterilized such as plastic or other artificial polymer material, so long as the material is biocompatible. A substrate can be any material that allows cells and/or tissue to adhere (or can be modified to allow cells and/or tissue to adhere or not adhere at select locations) and that allows cells and/or tissue to grow in one or more layers. Any number of materials can be used to form the substrate/surface, including, but not limited to, polyamides; polyesters; polystyrene; polypropylene; polyacrylates; polyvinyl compounds (e.g. polyvinylchloride); polycarbonate (PVC); polytetrafluoroethylene (PTFE); nitrocellulose; cotton; polyglycolic acid (PGA); cellulose; dextran; gelatin, glass, fluoropolymers, fluorinated ethylene propylene, polyvinylidene, polydimethylsiloxane, polystyrene, and silicon substrates (such as fused silica, polysilicon, or single silicon crystals), and the like. Also metals (gold, silver, titanium films) can be used.

As mentioned herein, in some instances the substrate may be modified to promote cellular adhesion and growth (e.g., coated with an adherence material). For example, a glass substrate may be treated with a protein (i.e., a peptide of at least two amino acids) such as collagen or fibronectin to assist cells in adhering to the substrate. In some embodiments, the proteinaceous material is used to define the location of a cellular island. The spot produced by the protein serves as a "template" for formation of the cellular island. Typically, a single protein will be adhered to the substrate, although two or more proteins may be used in certain embodiments. Proteins that are suitable for use in modifying a substrate to facilitate cell adhesion include proteins to which specific cell types adhere under cell culture conditions. For example, hepatocytes are known to bind to collagen. Therefore, collagen is well suited to facilitate binding of hepatocytes. Other suitable proteins include fibronectin, gelatin, collagen type IV, laminin, entactin, and other basement proteins, including glycosaminoglycans such as heparin sulfate. Combinations of such proteins also can be used.

The type of adherence material(s) (e.g., ECM materials, sugars, proteoglycans etc.) deposited in a spot will be determined, in part, by the cell type or types to be cultured. For example, ECM molecules found in the hepatic microenvironment are useful in culturing hepatocytes, the use of primary cells, and a fetal liver-specific reporter ES cell line. The liver has heterogeneous staining for collagen I, collagen III, collagen IV, laminin, and fibronectin. Hepatocytes display integrins $\beta1$, $\beta2$, $\alpha1$, $\alpha2$, $\alpha5$, and the nonintegrin fibronectin receptor Agp110 in vivo. Cultured rat hepatocytes display integrins α1, α3, α5, α1, and α6 µl, and their expression is modulated by the culture conditions.

The total number of spots on the substrate will vary depending on the substrate size, the size of a desired cellular island, and the spacing between cellular islands. Generally, the pattern present on the surface of the support will comprise at least 2 distinct spots, usually about 10 distinct spots, and more usually about 100 distinct spots, where the number of spots can be as high as 50,000 or higher. Typically, the spot will usually have an overall circular dimension (although other geometries such as spheroids, rectangles, squares and the like may be used) and the diameter will range from about 1 mm to 6 mm. The cellular islands may be spaced apart 400 µm to 1000 µm from edge to edge of the cellular islands. In some embodiments, the cellular islands may be spaced apart 400-500 µm, 500-600 µm, 600-700 µm, 700-800 µm, or 800-1000 µm.

By dispensing or printing onto the surfaces of multi-well culture plates, one can combine the advantages of the array approach with those of the multi-well approach. Typically, the separation between tips in standard spotting device is compatible with 96 well plates; one can simultaneously print each load in several wells. Printing into wells can be done using both contact and non-contact technology.

The invention can utilize robotic spotting technology to develop a robust, accessible method for forming cellular microarrays or islands of a defined size and spatial configuration on, for example, a cell culture substrate. As used herein, the term "microarray" refers to a plurality of addressed or addressable locations.

In one aspect, the invention provides methods and systems comprising a modified printing buffer used in a spotting device to allow for ECM deposition, and identifying microarray substrates that permit ECM immobilization. The methods and systems of the invention are useful for spotting substantially purified or mixtures of biological proteins, nucleic acids and the like (e.g., collagen I, collagen III, collagen IV, laminin, and fibronectin) in various combinations on a standard cell culture substrate (e.g., a microscope slide) using off-the-shelf chemicals and a conventional DNA robotic spotter.

In another aspect, the invention utilizes photolithographic techniques to generate cellular islands. Drawing on photolithographic micropatterning techniques to manipulate functions of rodent hepatocytes upon co-cultivation with stromal cells, a microtechnology-based process utilizing elastomeric stencils to miniaturize and characterize human liver tissue in an industry-standard multiwell format was used. The approach incorporates 'soft lithography,' a set of techniques utilizing reusable, elastomeric, polymer (Polydimethylsiloxane-PDMS) molds of microfabricated structures to overcome limitations of photolithography. In one aspect, the invention provides a process using PDMS stencils consisting of 300 µm thick membranes with through-holes at the bottom of each well in a 24-well mold. To micropattern all wells simultaneously, the assembly was sealed against a polystyrene plate. Collagen-I was physiosorbed to exposed polystyrene, the stencil was removed, and a 24-well PDMS 'blank' was applied. Co-cultures were 'micropatterned' by selective adhesion of canine hepatocytes to collagenous domains, which were then surrounded by supportive murine 3T3-J2 fibroblasts. The size (e.g., geometric dimension) of through-holes determined the size of collagenous domains and thereby the balance of homotypic (hepatocyte/hepatocyte) and heterotypic (hepatocyte/stroma) interactions in the microscale tissue. Similar techniques can be used to culture cellular islands of other parenchymal cell types.

The invention provides methods and systems useful for identifying optimal conditions for controlling cellular development and maturation by varying the size and/or spacing of a cellular island. For example, the methods and systems of the invention are useful for identifying optimal conditions that control the fate of cells (e.g., differentiating stem cells into more mature cells, maintenance of self-renewal, and the like).

The term "adherence material" is a material deposited on a substrate or chip to which a cell or microorganism has some affinity, such as a binding agent. The material can be deposited in a domain or "spot". The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, sugars, proteoglycans, or cellular receptors.

(vi) Cellular Components of the Co-Culture

Cells useful in the methods of the disclosure are available from a number of sources including commercial sources. For example, hepatocytes may be isolated by conventional methods (Berry and Friend, 1969, J. Cell Biol. 43:506-520) which can be adapted for canine liver biopsy or autopsy material. Typically, a cannula is introduced into the portal vein or a portal branch and the liver is perfused with calcium-free or magnesium-free buffer until the tissue appears pale. The organ is then perfused with a proteolytic enzyme such as a collagenase solution at an adequate flow rate. This should digest the connective tissue framework. The liver is then washed in buffer and the cells are dispersed. The cell suspension may be filtered through a 70 µm nylon mesh to remove debris. Hepatocytes may be selected from the cell suspension by two or three differential centrifugations.

Hepatocytes may also be obtained by differentiating pluripotent stem cell or liver precursor cells (i.e., hepatocyte precursor cells). The isolated hepatocytes may then be used in the culture systems described herein.

Cryopreserved canine hepatocytes and fresh human Kupffer cells can be obtained from either Bioreclamation Inc. (Westbury, N.Y.) or Triangle Research Labs, LLC (Research Triangle Park, N.C.). Stromal cells include, for example, fibroblasts obtained from appropriate sources as described further herein. Alternatively, the stromal cells may be obtained from commercial sources or derived from pluripotent stem cells using methods known in the art.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include, but are not limited to, trypsin, chymotrypsin, collagenase, elastase, and/or hyaluronidase, DNase, pronase, dispase and the like. Mechanical disruption can also be accomplished by a number of methods including, but not limited to, the use of grinders, blenders, sieves, homogenizers, pressure cells, or insonators. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis, fluorescence-activated cell sorting, and the like. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

The isolation of fibroblasts can, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be used in the culture systems of the disclosure.

Cancer tissue may also be cultured using the methods and co-culture system of the disclosure. For example, adenocarcinoma cells can be obtained by separating the adenocarcinoma cells from stromal cells by mincing tumor cells in HBSS, incubating the cells in 0.27% trypsin for 24 hours at 37° C. and further incubating suspended cells in DMEM complete medium on a plastic petri dish for 12 hours at 37° C. Stromal cells selectively adhered to the plastic dishes.

The co-cultures of the disclosure may be used to study cell and tissue morphology. For example, enzymatic and/or metabolic activity may be monitored in the culture system remotely by fluorescence or spectroscopic measurements on a conventional microscope.

In one aspect, a fluorescent metabolite in the fluid/media is used such that cells will fluoresce under appropriate conditions (e.g., upon production of certain enzymes that act upon the metabolite, and the like). Alternatively, recombinant cells can be used in the cultures system, whereby such cells have been genetically modified to include a promoter or polypeptide that produces a therapeutic or diagnostic product under appropriate conditions (e.g., upon zonation or under a particular oxygen concentration). For example, a hepatocyte may be engineered to comprise a GFP (green fluorescent protein) reporter on a P450 gene (CYPIA1). Thus, if a drug activates the promoter, the recombinant cell fluoresces. This is useful for predicting drug-drug interactions that occur due to upregulation in P450s.

The various techniques, methods, and aspects of the invention described above can be implemented in part or in whole using computer-based systems and methods. For example, computer implemented methods can be used in lithography techniques to design cellular islands.

The disclosure provides co-cultures of cells in which at least two types of cells are configured in a bounded geometric pattern on a substrate. Such micropatterning techniques are useful to modulate the extent of heterotypic and homotypic cell-cell contacts. In addition, co-cultures have improved stability and thereby allow chronic testing (e.g., chronic toxicity testing as required by the Food and Drug Administration for new compounds). Because micropatterned co-cultures are more stable than random cultures the use of co-cultures of the invention and more particularly micropatterned co-cultures provide a beneficial aspect to the cultures systems of the disclosure. Furthermore, because drug-drug interactions often occur over long periods of time the benefit of stable co-cultures allows for analysis of such interactions and toxicology measurements.

In one aspect, the invention provides an in vitro model of canine liver tissue that can be utilized for pharmaceutical drug development, basic science research, infectious disease research and in the development of tissue for transplantation. The invention provides compositions, methods, and co-culture systems that allow development of long-term human cultures in vitro. In addition, the compositions, methods and co-culture systems of the invention provide for the design of particular morphological characteristics by modifying cellular island size and distribution, and individual cell population ratios. The compositions, methods and co-culture systems of the disclosure have been applied to liver cultures and have shown that cellular island size and/or distribution contribute to induction of cellular metabolism that mimics in vivo metabolism. The results demonstrate that cellular distribution modulates gene expression and imply an important role in the maintenance of cell-specific metabolism (e.g., liver specific metabolism). In addition, considerations of the effect of such distribution in the design and optimization of current bioartificial support systems may serve to improve their function.

Certain materials, such as nylon, polystyrene, and the like, are less effective as substrates for cellular and/or tissue attachment. When these materials are used as the substrate it is advisable to pre-treat the substrate prior to inoculation with cells in order to enhance the attachment of cells to the substrate. For example, prior to inoculation with stromal cells and/or parenchymal cells, nylon substrates should be treated with 0.1 M acetic acid, and incubated in polylysine, FBS, and/or collagen to coat the nylon. Polystyrene could be similarly treated using sulfuric acid.

EXEMPLIFICATION

The working examples provided below are to illustrate, not limit, the disclosure. Various parameters of the scientific methods employed in these examples are described in detail below and provide guidance for practicing the disclosure in general.

In these particular working examples, dog hepatocytes are co-cultured with fibroblasts. Similar methods can be used to co-culture hepatocytes from other species. Although the invention has been generally described above, further aspects of the invention will be apparent from the specific disclosure that follows, which is exemplary and not limiting.

Example 1. Materials and Methods

Fibroblast Culture.

3T3-J2 fibroblasts were the gift of Howard Green (Harvard Medical School, Boston, Mass.). Cells were cultured at 37° C., 5% $CO_2$ in Dulbecco's Modified Eagle's Medium (DMEM) with high glucose, 10% (v/v) calf serum, and 1% (v/v) penicillin-streptomycin. BJ human foreskin stromal cells were purchased form American Type Culture Collection (ATCC), and were cultured in the same manner as the 3T3-J2 fibroblasts.

Hepatocyte Culture.

Primary dog hepatocytes were purchased in suspension from either Bioreclamation Inc. (Westbury, N.Y.) or Triangle Research Labs, LLC (Research Triangle Park, N.C.). Upon receipt, dog hepatocytes were pelleted via centrifugation at 50×g for 5 minutes at 4° C. The supernatant was discarded, cells were re-suspended in hepatocyte culture medium, and viability was assessed using trypan blue exclusion (70-90%).

Hepatocyte-Fibroblast Co-Cultures.

Standard Becton Dickenson 24 well multi-well cell culture plates were pre-coated with rat tail collagen and patterned to create islands of collagen (to which the dog hepatocytes adhere) as previously described in U.S. Pat. No. 8,449,285. 500 µm islands on 1200 µm centers were prepared as described in U.S. Pat. No. 8,449,285, however PDMS patterns for the 3, 4, and 5 mm islands were prepared by pouring the PDMS into molds machined into a Teflon block.

In order to create micropatterned co-cultures, hepatocytes were seeded in serum-free hepatocyte medium on collagen-patterned 24-well cell culture plates, resulting in a hepatocyte pattern due to selective cell adhesion. The cells were washed with media 2 to 6 hours later to remove unattached cells and incubated with serum supplemented hepatocyte medium overnight. 3T3-J2 or BJ fibroblasts were seeded in serum-supplemented fibroblast medium 12-24 hours later to create co-cultures. Culture medium was replaced with hepatocyte medium 24 hours after fibroblast seeding and subsequently replaced every one to two days. Spent media was stored for biochemical assays.

Biochemical Assays.

Spent media was stored at −20° C. Urea concentration was assayed using a colorimetric endpoint assay utilizing diacetylmonoxime with acid and heat (Stanbio Labs, Boerne, Tex.). Albumin content was measured using enzyme linked immunosorbent assays (MP Biomedicals, Irvine, Calif.) with horseradish peroxidase detection and 3, 3',5, 5"-tetramethylbenzidine (TMB, Fitzgerald Industries, Concord, Mass.) as a substrate. Cyp3A4 assays were performed using Promega Inc. kits.

Example 2. Micropatterned Canine Hepatocyte-Stromal Cell Co-Cultures

Figure 2:
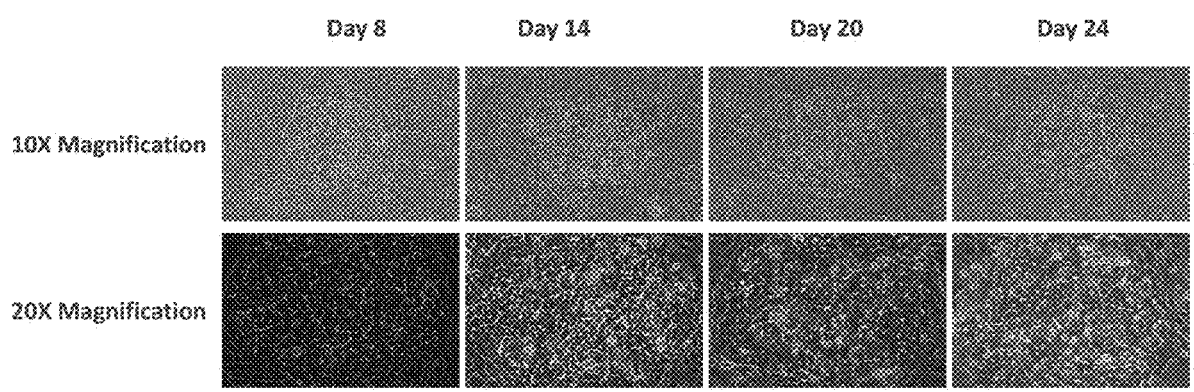
FIG. 2 shows island integrity and morphology in the human HepatoPac™ platform. 500 micron islands, with 1200 micron center-to-center spacing, support proper morphology and island integrity for up to 4 weeks in human, rat, and monkey hepatoctytes (human shown).

The HepatoPac™ platform is shown in FIG. 1. The standard HepatoPac™ architecture used for human, monkey, and rat hepatocytes consists of 500 µm hepatocyte islands, spaced 1200 µm apart (center-to-center). 3T3-J2 murine fibroblasts used as stromal cells for human, rat and monkey formats. The standard HepatoPac™ architecture allows for optimal hepatocyte island integrity and morphology for at least 24 days with human, rat, and monkey hepatocytes. FIG. 2 shows island morphology for human hepatocytes in the standard HepatoPac™ architecture at days 8, 14, 20, and 24 in culture.

Figure 3:
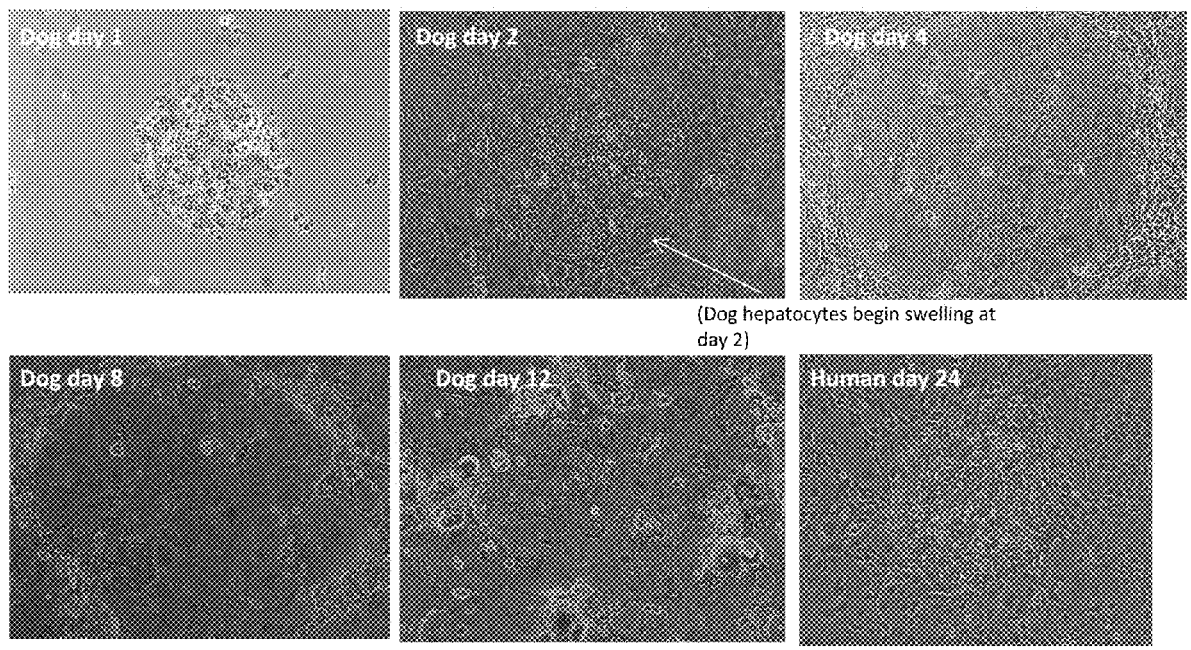
FIG. 3 shows that dog hepatocytes are not supported by the standard HeptoPac™ format. Dog hepatocytes are not supported by 500 µm islands (1200 µm center-to-center spacing), with hypertrophy of hepatocytes and complete loss of island integrity by day 12. The human day 24 island in the standard format is shown for comparison. All panels are at 10× magnification.

Surprisingly, application of the standard HepatoPac™ format to dog hepatocyte cell culture resulted in early and extreme morphological changes to the architecture of the cell culture (loss of uniform island shape) and extreme hypertrophy of the hepatocytes. The dog hepatocytes showed significant hypertrophy and motility in the standard HepatoPac™ format, resulting in complete loss of island integrity by Day 12 of culture. FIG. 3 shows dog hepatocyte morphology and island integrity in the standard format at days 1, 2, 4, 8, and 12 of culture. A human hepatocyte island in the standard format at day 24 of culture, with optimal island integrity, is shown for comparison in the bottom right panel of FIG. 3.

Example 3. Influence of Different Stromal Cell Populations on Dog Hepatocytes

As discussed above in Example 1, dog hepatocytes were found to undergo significant morphological changes in the standard HepatoPac™ format. Hepatocyte growth factor (HGF) was implicated as one of the contributing factors causing dog hepatocyte hypertrophy and motility in the co-culture (data not shown). HGF knockdown via dexamethasone and TGFB2 resulted in diminished hypertrophy of the hepatocytes. Soluble human HGF alone did not result in hepatocyte hypertrophy in sandwich cultures (data not shown). In summation, chemical inhibition (for example, via dexamethasone and TGFB2) of HGF secretion in the standard HepatoPac™ format is sufficient to abrogate hepatocyte hypertrophy. The reduction in HGF by tryptanthrin and UDCA also translated to decreased dog hepatocyte hypertrophy. HGF alone is not sufficient to cause hypertrophy suggesting the importance of cell-cell communication/matrix interactions.

Figure 4:
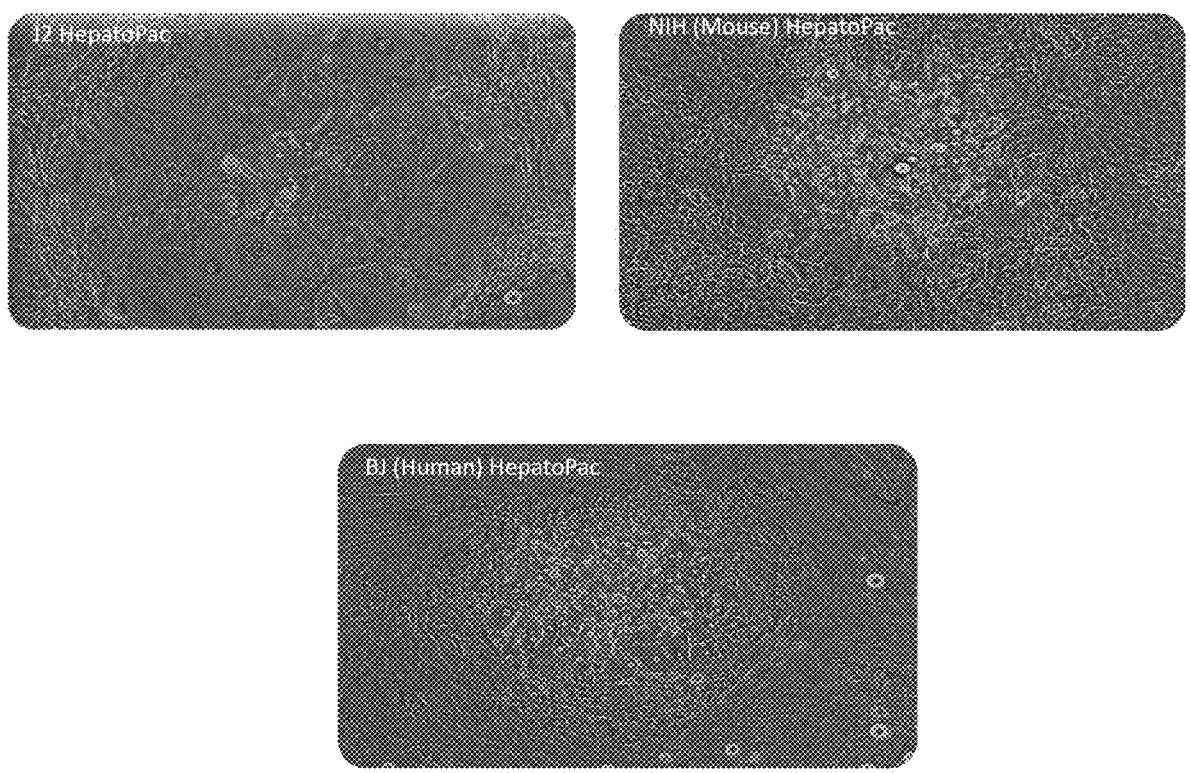
FIG. 4 shows the effect of different stromal cell populations on dog hepatocyte hypertrophy. The use of human BJ stromal cells (lower center panel) reduces hypertrophy of hepatocytes compared to murine 3T3-J2 stromal cells (top right panel). Day 6 morphology is shown.
Figure 5:
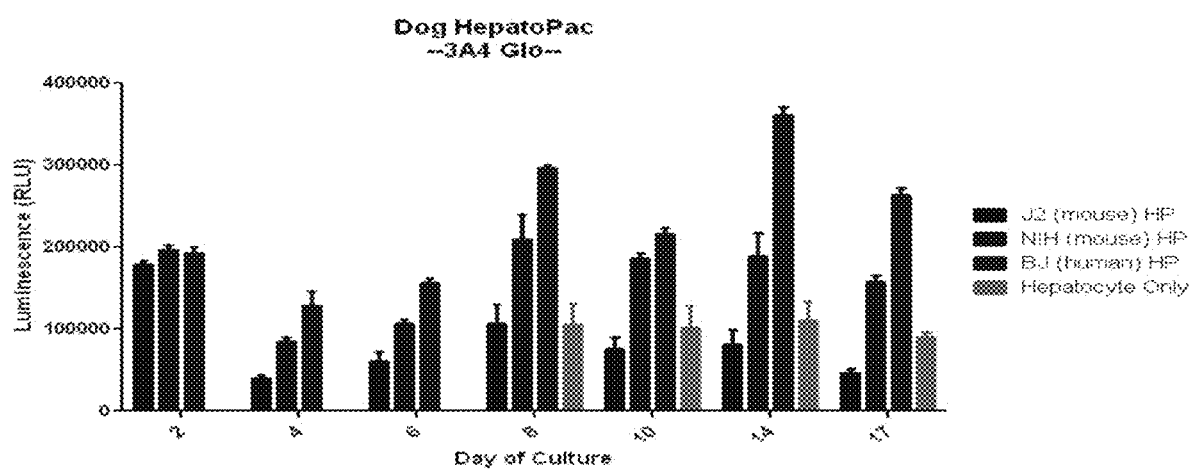
FIG. 5 shows the effect of different stromal cell populations on dog hepatocyte functionality, as measured by CYP3A4 activity. BJ stromal cells support higher hepatocyte functionality compared to murine 3T3-J2 or murine NIH stromal cells.

HGF was used as a biomarker to screen for an alternative to the murine 3T3-J2 fibroblasts used in the human, rat, and monkey HepatoPac™ co-cultures. Human foreskin BJ fibroblasts were found to have low production of HGF. The use of BJ fibroblasts as stromal cells in the co-culture reduced dog hepatocyte hypertrophy compared to 3T3-J2 stromal cells (FIG. 4). Murine NIH 3T3 fibroblasts were also found to decrease dog hepatocyte hypertrophy. FIG. 4 shows the island architecture and hepatocyte morphology at day 6 of co-culture with 3T3-J2, BJ, or NIH 3T3 stromal cells. Hepatocyte functionality was also assessed. FIG. 5 shows the effect of murine 3T3-J2, murine NIH or human BJ stromal cells on dog hepatocyte functionality in co-culture at days 2, 4, 6, 8, 10, 14, and 17 of culture. BJ stromal cells promoted higher levels of dog hepatocyte functionality than 3T3-J2 or NIH 3T3 stromal cells, as demonstrated by CYP3A4 activity (FIG. 5). Therefore, in addition to reducing hepatocyte hypertrophy, BJ stromal cells also maintained higher levels of hepatocyte functionality.

Figure 6:
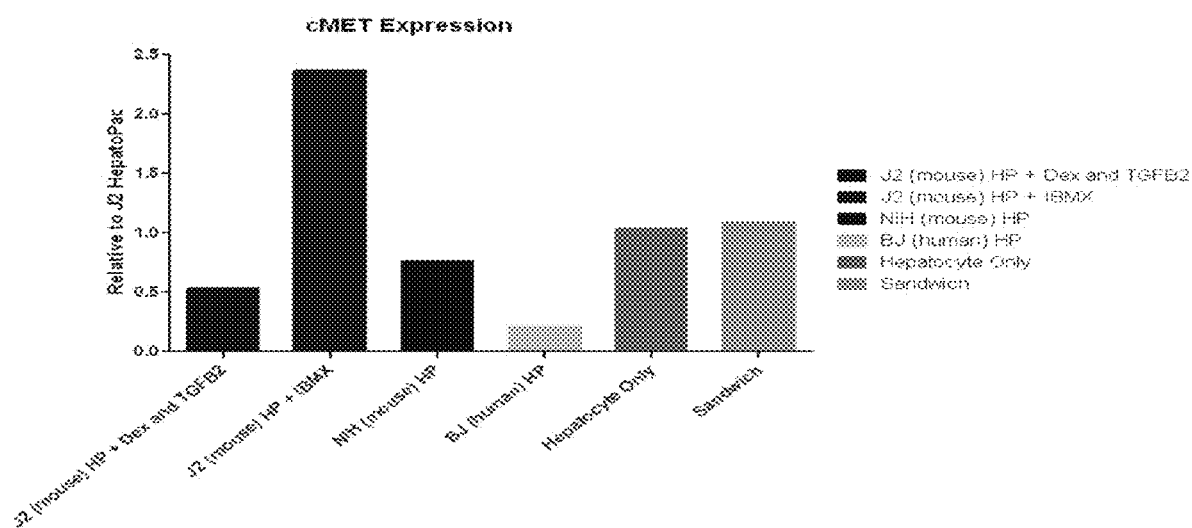
FIG. 6 shows the effect of different stromal cell populations on expression levels of HGF receptor c-Met in dog hepatocytes, in the presence or absence of known chemical inhibitors of HGF. The decrease in c-Met expression levels is greatest when dog hepatocytes are cultured with human BJ stromal cells, compared to known chemical inhibitors and standard HepatoPac™ culture models with murine 3T3-J2 stromal cells.

The effect of the different stromal cells on HGF receptor c-Met was studied. BJ and NIH 3T3 stromal cells both resulted in decreased c-Met expression in dog hepatocyte co-cultures. The reduction in c-Met expression was greatest when dog hepatocytes are cultured with BJ stromal cells, compared to known chemical inhibitors such as dexamethasone or TGFB2 and standard culture models (FIG. 6). IBMX was used as a negative chemical control.

Example 4. Influence of Island Size on Dog Hepatocytes

Figure 7:
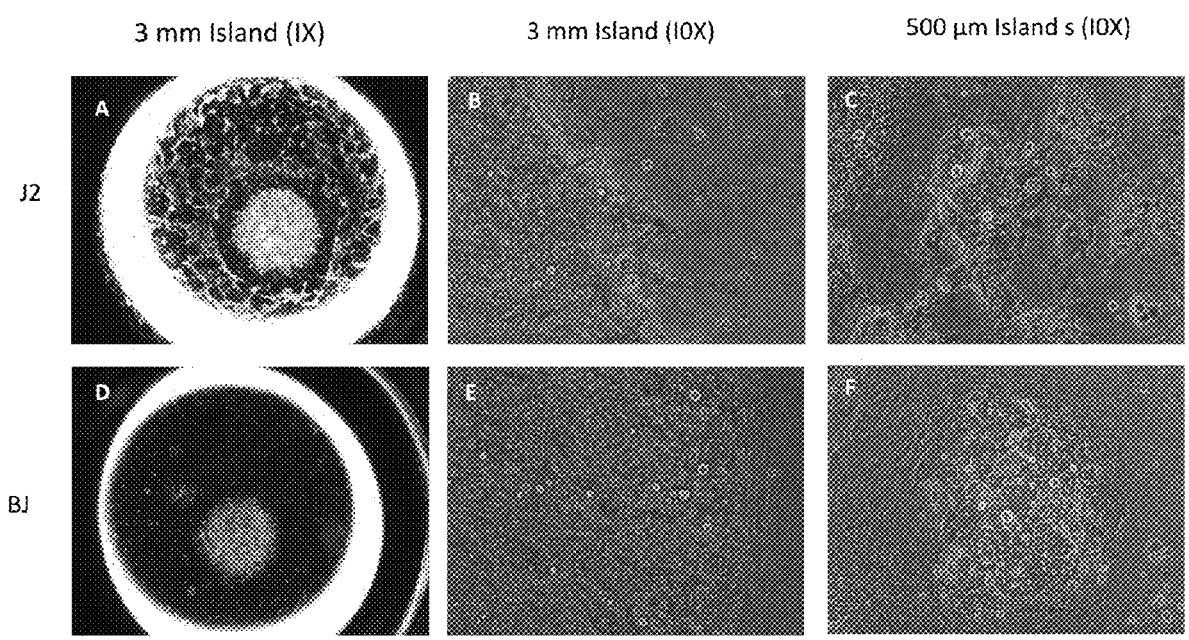
FIG. 7 shows the effect of island width or diameter and stromal cell population on dog hepatocyte morphology and motility. Hypertrophy and motility of dog hepatocytes was limited in 3 mm islands cultured with human BJ stromal cells (panels D & E) compared to murine 3T3-J2 stromal cells (panels A & B). 500 µm islands of dog hepatocytes cultured with 3T3-J2 or BJ stromal cells exhibit hypertrophy and motility (panels C and F, respectively). Day 13 morphology is shown.
Figure 8:
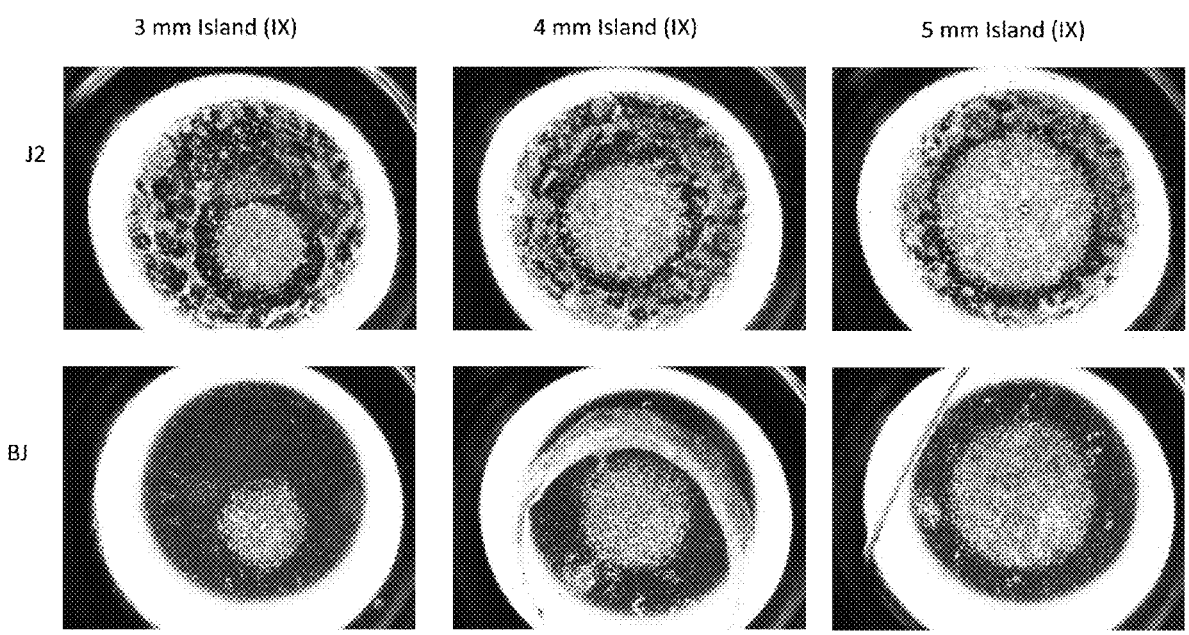
FIG. 8 shows the effect of island width or diameter and stromal cell population on dog hepatocyte morphology and motility. Hypertrophy and motility was limited in all larger island sizes (3-5 mm) with little or no "Halo" effect when dog hepatocytes are cultured with human BJ stromal cells, as compared to dog hepatocytes cultured with murine 3T3-J2 stromal cells. Day 22 morphology is shown.

The effect of island width or diameter on dog hepatocytes in micropatterned co-cultures was examined. The standard HepatoPac™ island size of 500 µm served as the control. Island sizes of 3 mm, 4 mm, and 5 mm were tested for their ability to improve canine hepatocyte culture, in combination with either the standard 3T3-J2 stromal cells (control) or BJ stromal cells. Hypertrophy and motility of dog hepatocytes was observed at various time points up to day 22 of co-culture. FIG. 7 shows the hepatocyte morphology and island architecture at day 13 of co-culture using island sizes of 3 mm and 500 μm. Hypertrophy and motility of dog hepatocytes was limited in 3 mm islands cultured with BJ stromal cells (FIGS. 7D and 7E) compared to 3T3-J2 stromal cells (FIGS. 7A and 7B). 500 μm islands of dog hepatocytes culture with J2 or BJ stromal cells exhibit hypertrophy and motility (FIGS. 7C and 7F, respectively). FIG. 8 shows hepatocyte morphology and island architecture using island sizes of 3 mm, 4 mm, and 5 mm at day 22 of the co-culture. Hypertrophy and motility was limited in all larger island sizes (3-5 mm) with little or no "halo" effect when dog hepatocytes are cultured with BJ stromal cells, as compared to dog hepatocytes cultured with 3T3-J2 stromal cells (FIG. 8).

Figure 9A:
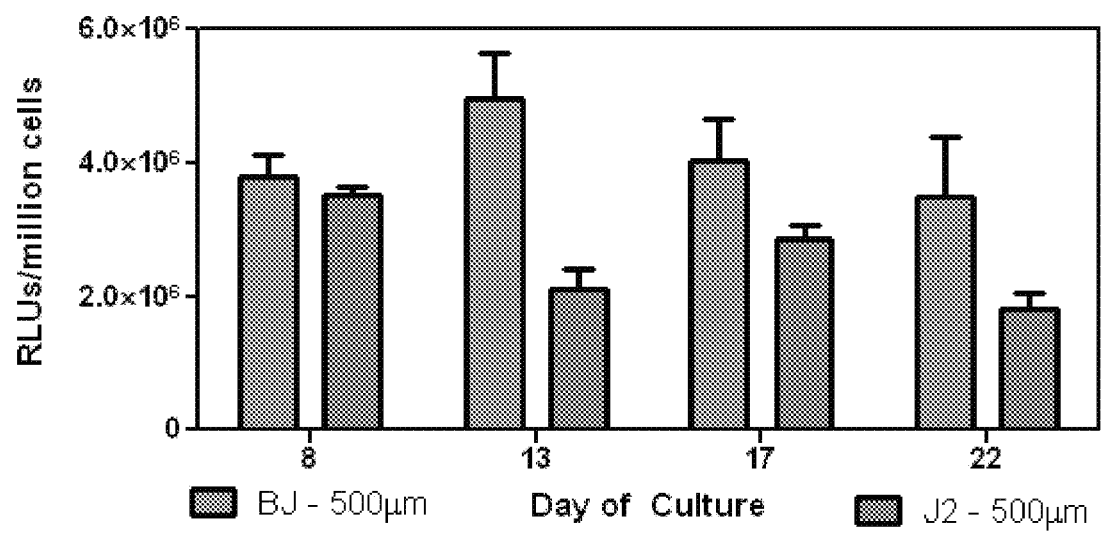
FIGS. 9A and 9B show the effect of different stromal cell populations and island width or diameter, respectively, on hepatocyte functionality, as demonstrated by CYP3A4 activity. Dog hepatocytes cultured on 3 mm islands exhibit higher functionality (CYP3A4 activity) than hepatocytes cultured on 500 µm islands.
Figure 9B:
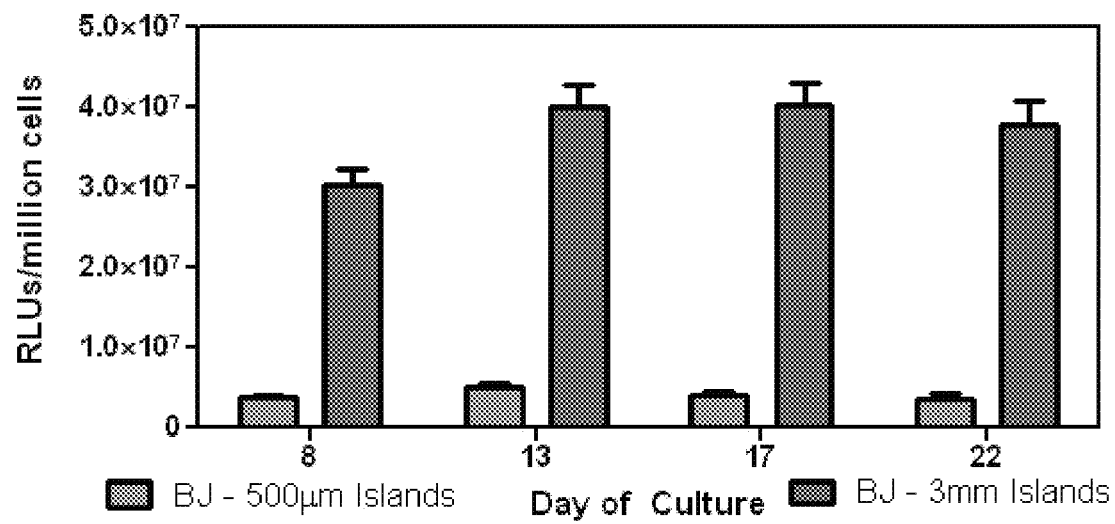
Figure 10A:
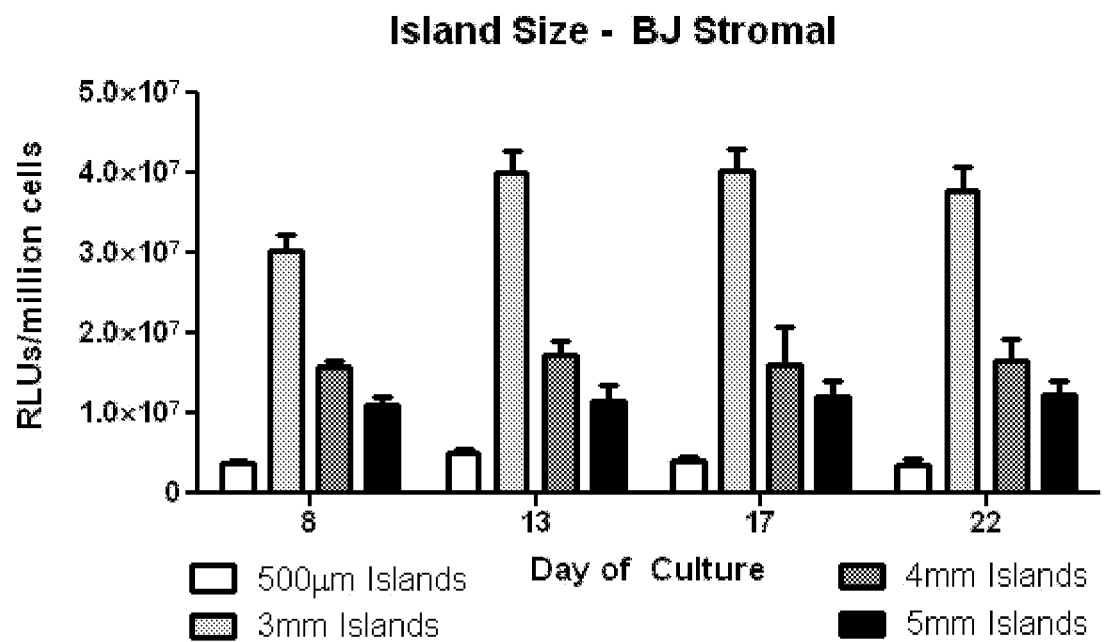
FIGS. 10A and 10B show the effect of human BJ stromal cells and murine 3T3-J2 stromal cells, respectively, on hepatocyte functionality at various island widths or diameters, as demonstrated by CYP3A4 activity. Dog hepatocytes cultured on 3 mm islands exhibit higher functionality (CYP3A4 activity) than hepatocytes cultured on 500 µm, 4 mm or 5 mm islands.
Figure 10B:
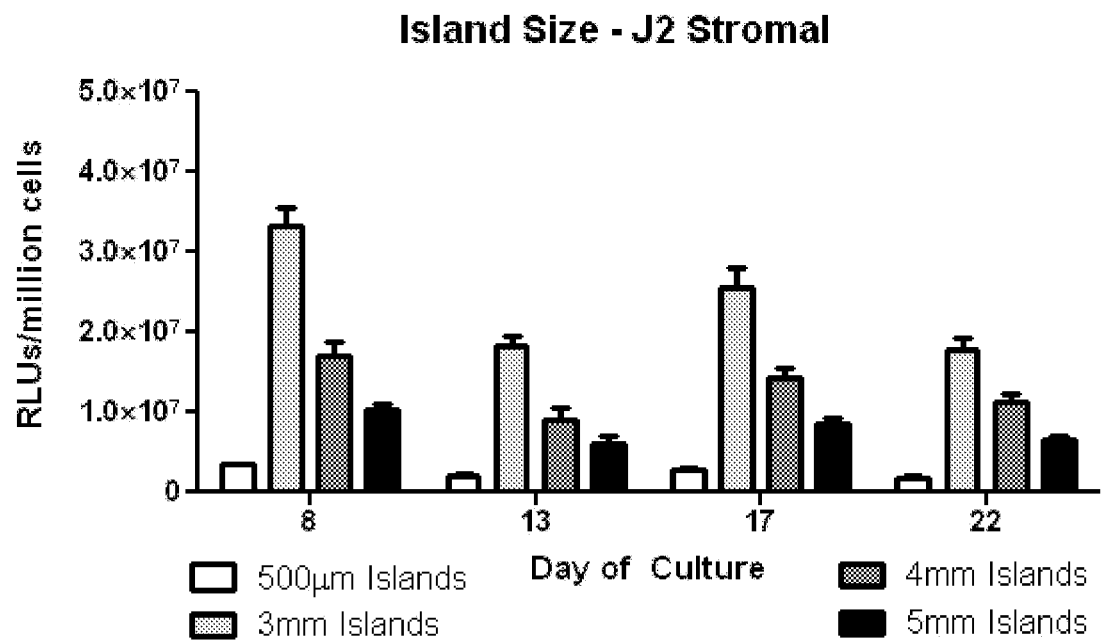
Figure 11A:
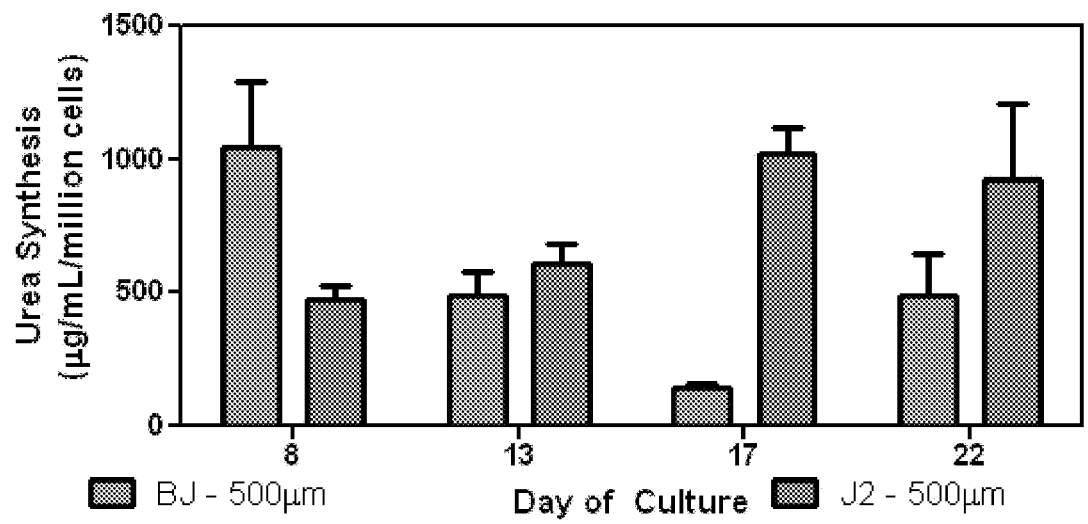
FIGS. 11A and 11B show the effect of different stromal cell populations and island width or diameter, respectively, on hepatocyte functionality as demonstrated by urea synthesis. Dog hepatocytes cultured on 3 mm islands exhibit higher functionality (urea synthesis) than hepatocytes cultured on 500 µm islands.
Figure 11B:
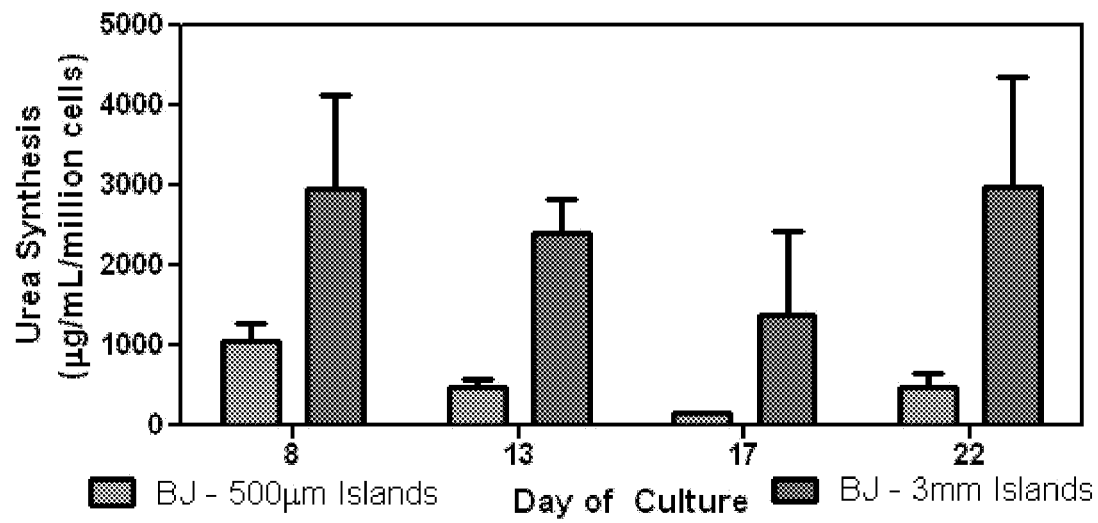

Hepatocyte functionality in the various formats was tested using CYP3A4 activity and urea synthesis as markers of hepatocyte functionality. FIGS. 9 and 10 show the effect of stromal cell population selection and island size on hepatocyte functionality, as demonstrated by CYP3A4 activity, at days 8, 13, 17, and 22 of culture. FIG. 9A shows the effect of stromal cell population on 500 μm islands and it can be seen that BJ stromal cells lead to improved hepatocyte functionality, compared to 3T3-J2 stromal cells. FIG. 9B shows the effect of island size on hepatocyte functionality in the presence of BJ stromal cells. Dog hepatocytes cultured on 3 mm islands exhibited higher functionality (CYP3A4 activity) than hepatocytes cultured on 500 μm islands. FIGS. 10A and 10B show the effect of island size in combination with either BJ stromal cells or 3T3-J2 cells. Dog hepatocytes cultured on 3 mm islands exhibited higher functionality (CYP3A4 activity) than hepatocytes cultured on 500 μm, 4 mm or 5 mm islands. FIG. 11 shows the effect of stromal cell population selection and island size on hepatocyte functionality, as demonstrated by urea synthesis, at days 8, 13, 17, and 22 of culture. Dog hepatocytes cultured on 3 mm islands exhibited higher functionality (urea synthesis) than hepatocytes cultured on 500 μm islands.

To summarize, the effect of stromal cell population and island size on dog hepatocyte micropatterned co-cultures was examined. Data presented here demonstrates that when dog hepatocytes are co-cultured with 3T3-J2 stromal cells, increasing island size reduces hypertrophy and promotes better island integrity but hypertrophy is still present. 3 mm islands appear to have wider bands of hypertrophy than 5 mm islands ("halo"). The data further demonstrates that when dog hepatocytes are co-cultured with BJ stromal cells, increasing island size reduces hypertrophy, and promotes better island integrity. Changes to hepatocyte morphology appear less drastic at the edge of the island, when cultured with BJ instead of J2 stromal cells. Hypertrophy was limited in all larger island sizes (3-5 mm) with little or no "halo" effect. In conclusion, increasing the diameter of the islands in the co-culture, alone or in addition to switching to BJ stromal cells, allowed the co-cultures to maintain a stable architecture, eliminating hepatocyte hypertrophy for the vast majority of canine hepatocytes, and to maintain higher levels of biological functionality than the prior micropatterned co-culture architecture with 3T3-J2 murine stromal cells.

While specific embodiments of the subject matter have been discussed, the above specification is illustrative and not restrictive. Many variations will become apparent to those skilled in the art upon review of this specification and are within the scope of the invention.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A micropatterned co-culture comprising:
   (a) a population of canine hepatocytes defining a cellular island, wherein the cellular island comprises a diameter or width from about 750 microns to about 6 mm; and
   (b) a population of stromal cells, wherein the stromal cells define a geometric border of the cellular island,
   wherein the canine hepatocytes maintain long-term functional stability.

2. The micropatterned co-culture of claim 1, wherein the stromal cells do not induce canine hepatocyte hypertrophy or motility.

3. The micropatterned co-culture of claim 1, wherein the stromal cells secrete a level of hepatocyte growth factor (HGF) that does not induce canine hepatocyte hypertrophy.

4. The micropatterned co-culture of claim 1, wherein the stromal cells secrete a level of HGF that does not induce canine hepatocyte motility.

5. The micropatterned co-culture of claim 1, wherein the stromal cells exhibit a decreased production or secretion of HGF relative to 3T3-J2 murine fibroblasts.

6. The micropatterned co-culture of claim 1, further comprising an HGF-inhibiting agent.

7. The micropatterned co-culture of claim 6, wherein the HGF-inhibiting agent is selected from the group consisting of dexamethasone and TGFB2.

8. The micropatterned co-culture of claim 1, wherein functional stability of the canine hepatocytes is determined by measuring an activity selected from gene expression, cell function, metabolic activity, morphology, and a combination thereof, of the hepatocytes.

9. The micropatterned co-culture of claim 8, wherein the metabolic activity is selected from CYP3A4 activity, urea synthesis, and albumin secretion.

10. The micropatterned co-culture of claim 1, wherein the stromal cells are selected from the group consisting of human cells, rat cells, mouse cells, monkey cells, dog cells, fish cells and guinea pig cells.

11. A method for producing a micropatterned co-culture containing canine hepatocytes, the method comprising:
   (a) spotting an adherence material on a substrate at spatially different locations, each spot having a defined geometric pattern, wherein the defined geometric pattern comprises a diameter or width of about 750 microns to 6 mm;
   (b) contacting the substrate with a population of canine hepatocytes that selectively adhere to the adherence material and/or substrate;
   (c) culturing the canine hepatocytes on the substrates to generate a plurality of cellular islands; and
   (d) contacting the substrate with a stromal cell population that adheres to the substrate at a location different than the hepatocyte population, wherein the cells of the stromal cell population define a geometric border of the cellular island, to generate a hepatocyte-stromal cell co-culture, wherein the canine hepatocytes maintain long-term functional stability.

12. A method of determining the interaction of one or more test compounds with canine hepatocytes comprising:
   a) contacting a micropatterned co-culture comprising canine hepatocytes and stromal cells with one or more test agents, wherein the canine hepatocytes define a cellular island comprising a diameter or width from about 750 microns to about 6 mm and the stromal cells define a geometric border of the cellular island; and
   b) measuring a characteristic of the one or more test compounds or an activity of the hepatocytes, wherein the characteristic or activity measured in (b) indicates the interaction of one or more test compounds with hepatocytes, and
   wherein the canine hepatocytes maintain long-term functional stability.

13. The method of claim 12, wherein the stromal cells do not induce canine hepatocyte hypertrophy or motility.

14. The method of claim 12, wherein the stromal cells secrete a level of hepatocyte growth factor (HGF) that does not induce canine hepatocyte hypertrophy.

15. The method of claim 12, wherein the stromal cells secrete a level of HGF that does not induce canine hepatocyte motility.

16. The method of claim 12, wherein the stromal cells exhibit a decreased production or secretion of HGF relative to 3T3-J2 murine fibroblasts.

17. The method of claim 12, wherein the activity of the hepatocytes is selected from gene expression, cell function, metabolic activity, morphology, cytokine secretion, protein or metabolite secretion, and a combination thereof.

18. The method of claim 12, wherein the hepatocytes maintain long-term functional stability for at least 10 days.

19. The micropatterned co-culture of claim 1, wherein the micropatterned co-culture further comprises one or more populations of non-parenchymal cells.

20. The micropatterned co-culture of claim 19, wherein the non-parenchymal cells are Kupffer cells.

21. The micropatterned co-culture of claim 19, wherein the non-parenchymal cells are selected from the group consisting of human cells, rat cells, mouse cells, monkey cells, dog cells, fish cells and guinea pig cells.

22. The micropatterned co-culture of claim 1, wherein the canine hepatocytes maintain long-term functional stability for at least 10 days.

* * * * *